United States Patent
Eichler

(10) Patent No.: US 10,070,804 B2
(45) Date of Patent: Sep. 11, 2018

(54) APPARATUS AND METHOD FOR THE COLLECTION OF SAMPLES OF EXHALED AIR

(75) Inventor: Rudiger Eichler, Zellingen (DE)

(73) Assignee: Circassia AB, Uppsala (SE)

( * ) Notice: Subject to any disclaimer, the term of this patent is extended or adjusted under 35 U.S.C. 154(b) by 901 days.

(21) Appl. No.: 13/989,491

(22) PCT Filed: Dec. 7, 2011

(86) PCT No.: PCT/EP2011/072116
§ 371 (c)(1),
(2), (4) Date: May 24, 2013

(87) PCT Pub. No.: WO2012/076614
PCT Pub. Date: Jun. 14, 2012

(65) Prior Publication Data
US 2013/0245483 A1 Sep. 19, 2013

(30) Foreign Application Priority Data

Dec. 8, 2010 (DE) .......... 10 2010 054 397

(51) Int. Cl.
*A61B 5/08* (2006.01)
*A61B 5/097* (2006.01)
(Continued)

(52) U.S. Cl.
CPC .............. *A61B 5/097* (2013.01); *A61B 5/082* (2013.01); *G01N 33/497* (2013.01);
(Continued)

(58) Field of Classification Search
CPC ....... A61B 5/082; A61B 5/097; A61B 5/6819; A61B 5/682; G01N 33/497
See application file for complete search history.

(56) References Cited

U.S. PATENT DOCUMENTS

| 4,688,568 | A |   | 8/1987 | Frass et al. |
| 5,293,875 | A | * | 3/1994 | Stone ............ G01N 33/497 |
|           |   |   |        | 128/204.22 |

(Continued)

FOREIGN PATENT DOCUMENTS

| CA | 2669385 | 5/2008 |
| EP | 1800707 | 6/2007 |

OTHER PUBLICATIONS

International Search Report from corresponding International Application No. PCT/EP2011/072116, dated Jul. 30, 2012.

*Primary Examiner* — Puya Agahi
(74) *Attorney, Agent, or Firm* — Renner, Otto, Boisselle & Sklar, LLP

(57) ABSTRACT

An apparatus for the collection of samples of exhaled air during normal respiration, comprising a flow generator, an orally insertable exhalation air receiver, and a device for isolating the nasal airways, wherein the apparatus further comprises: a sensor for detecting a change in a parameter representing the change from inhalation to exhalation and to transmit said change as a signal; a control unit adapted to receive said signal and to control said device for isolating the nasal airways; wherein the flow generator is connected to or integrated with the exhalation air receiver. A method of collecting samples of exhaled air during normal respiration conditions, comprising the steps of: detecting a change in a parameter representing the change from inhalation to exhalation and transmitting said change as a signal; receiving said signal in a control unit; activating a device for isolating the nasal airways; activating a flow generator connected to an exhalation air receiver; and collecting a sample of exhaled air during exhalation when the nasal airways are isolated.

6 Claims, 11 Drawing Sheets

(51) Int. Cl.
   *G01N 33/497*    (2006.01)
   *A61B 5/00*      (2006.01)
   *A61B 5/113*     (2006.01)

(52) U.S. Cl.
   CPC ........... *A61B 5/0813* (2013.01); *A61B 5/1135* (2013.01); *A61B 5/682* (2013.01); *A61B 5/6819* (2013.01); *A61B 5/6833* (2013.01); *A61B 2503/04* (2013.01); *A61B 2503/06* (2013.01)

(56) References Cited

U.S. PATENT DOCUMENTS

| | | | |
|---|---|---|---|
| 2005/0177056 A1* | 8/2005 | Giron | A61M 16/0666 600/543 |
| 2007/0039614 A1* | 2/2007 | Djupesland | A61M 15/009 128/200.23 |
| 2007/0095347 A1 | 5/2007 | Hickle et al. | |
| 2008/0006267 A1* | 1/2008 | Cahill | A61F 5/56 128/201.18 |
| 2008/0107569 A1* | 5/2008 | Stefano | A61B 5/097 422/84 |
| 2008/0142019 A1 | 6/2008 | Lewis et al. | |
| 2008/0216838 A1 | 9/2008 | Wondka | |
| 2008/0221471 A1 | 9/2008 | Djupesland et al. | |
| 2008/0275355 A1 | 11/2008 | Namjou-Khaless et al. | |
| 2009/0194100 A1* | 8/2009 | Minagi | A61F 5/08 128/200.24 |

\* cited by examiner

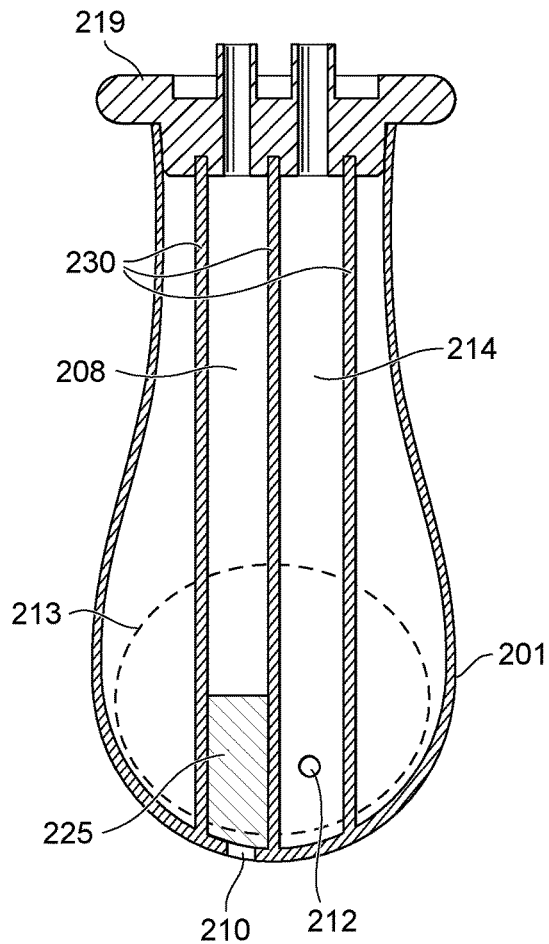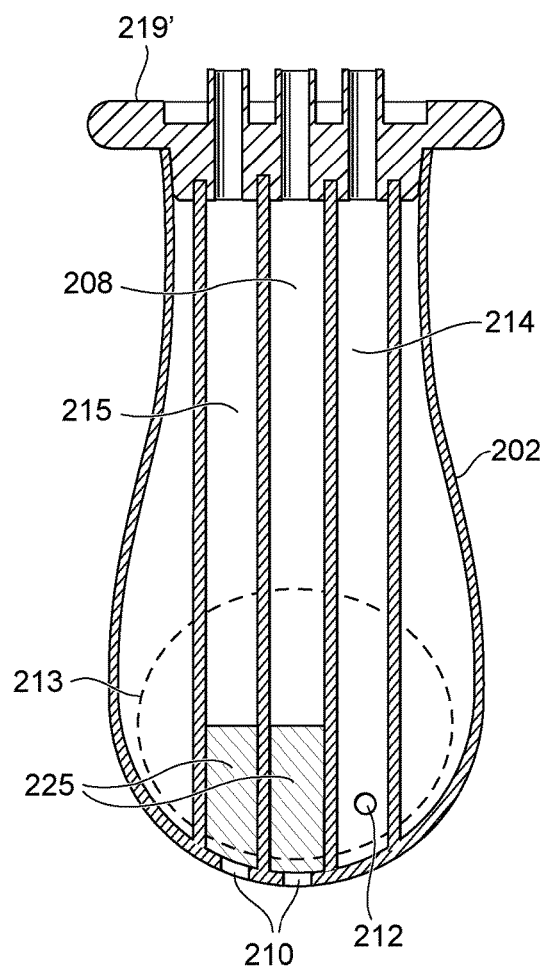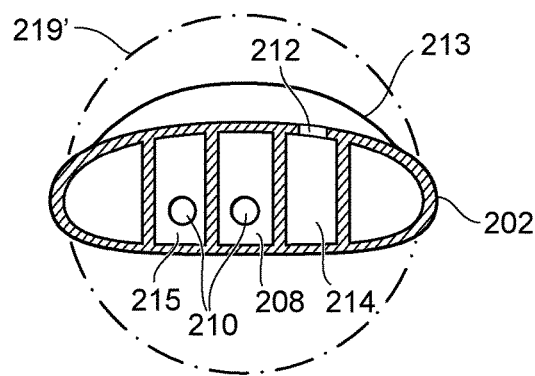

APPARATUS AND METHOD FOR THE COLLECTION OF SAMPLES OF EXHALED AIR

TECHNICAL FIELD

The invention relates to devices and methods for the collection of samples of exhaled air under normal respiration conditions, in particular in subjects unable to follow instructions or unable to comply with the requirements for the collection of a sample. Examples of such subjects include, but are not limited to infants and small children, as well as disabled, unconscious, or elderly patients. The collection of samples of exhaled air is preferably performed for the purpose of determining the presence and/or concentration of a component of said exhaled air.

BACKGROUND

It is known that there are numerous components in exhaled air that may provide useful insights into metabolic processes in certain diseases, as well as function as indicators of certain diseases and even indicating the presence of certain disease causing agents. The concentrations of such components have been studied in great detail in both research and clinical settings. Based on these insights, the concentration values aid in the establishing of a diagnosis, and have proven useful to monitor the well being of a patient, etc. Two examples of clinically interesting components in exhaled air are inorganic and organic gaseous compounds. Examples of gaseous compounds present in exhaled air include nitrogen monoxide, here nitric oxide (NO), carbon dioxide ($CO_2$), oxygen ($O_2$), and volatile organic compounds. Further examples are more or less complex chemical compounds and biomolecules that can be detected in exhaled breath condensate, such as hydrogen peroxide, S-nitrosothiols, nitrotyrosine, proteins, cytokines, and macromolecules, to mention only a few.

An important example is NO, which since it was found to be a diagnostic marker of inflammation in the early 1990-ies, has become the focus of much research. Different techniques and sensors have been suggested for use in the determination of NO concentration. Examples include, but are not limited to chemiluminescence, semiconductor-based sensors, electrochemical sensors, and polymer-based sensors.

The American Thorax Society (ATS) and the European Respiratory Society (ERS) have published guidelines for the standardized examination of the lung function and of the determination of lung-function markers (See for example "An Official ATS Clinical Practice Guideline: Interpretation of Exhaled Nitric Oxide Levels (FENO) for Clinical Applications", in Am. J. Respir. Crit. Care Med. 2011, 184: 602-615).

The main emphasis of the ATS/ERS guidelines is the examination and demonstration of endogenous NO of the deeper lung areas in the exhaled air (exhalate). The guidelines indicate various standards in this regard for the various measuring methods such as the online or offline measuring of adults, but also of children.

One problem in the determination of NO in exhaled air is the fact that the fractionated, endogenous NO (FENO) that stems from the deeper-lying areas of the lung, is present in clearly lower concentrations than nasal NO, so that the measured values of FENO are offset by the admixture of nasal NO.

The ATS/ERS guidelines take this circumstance into account and stipulate making the patient exhale against an expiratory resistance of at least 5 cm $H_2O$. The velum will be closed and the nasopharynx isolated when the patient exhales against such a resistance.

The ATS/ERS guidelines also take account of the fact that the concentration of FENO is heavily dependent on the expiratory flow, because the greater the expiratory flow is, the lower the measurable FENO concentrations in the exhaled air. Therefore, the guidelines stipulate in this regard that the patient be allowed to exhale at a constant exhalation rate of preferably 50 ml/s. To this end the patient is requested to independently maintain the exhalation rate constant at a given level with the aid of an optical display. Flow meters, pressure indicators and also computer-animated graphics serve as displays.

In addition, the ATS/ERS guidelines require that the measured values be recorded in the range of a NO plateau. However, since the NO plateau is adjusted only offset in time after the beginning of the exhalation, the patient must complete a constant exhalation over a period of 4 or 10 seconds, depending on the age of the patient. The standard methods stipulated by the ATS and the ERS are recommended for adults and children above the age of 6 years.

Collectors of samples of respiratory gas are known in the state of the art for online as well as for offline measuring.

One sample collector for the offline measuring of FENO, using which respiratory gas samples can be collected under the required ATS/ERS conditions, is disclosed in the ATS/ERS guidelines (2011). This collector consists of a guide tube with mouthpiece that comprises a NO filter on the inhalation side through which the patient inhales surrounding air. The exhalation takes place against an expiratory resistance generated by modification in the mouthpiece. The exhaled air is collected in a MYLAR® bag. In order to maintain the stipulated ATS/ERS standard, the sample collector is also equipped with a pressure indicator assisting the patient in executing the required breathing maneuver under self-control.

In another offline sample collector, also disclosed in the ATS/ERS guidelines, the exhaled air is fractionated in that at first the dead-space component from the upper lung areas is separated in a catch bag. The fraction from the lower lung areas is subsequently trapped in a second collection container and later supplied to the analysis.

US 2008/0221471 shows an apparatus for the collection of airway gases, including NO, from a subject comprising a first means for producing closure of the velum of the subject, and a second means for the collection of airway gases, wherein the first and second means need not be integrated with each other. It appears from the disclosure that said means for producing closure of the velum rely on the presence of an adjustable/changeable resistor optionally followed by a pressure gauge, and that the subject is instructed to try to keep a stable pressure corresponding to a desired flow during exhalation. The disclosure of US 2008/0221471 also discusses nasal NO-measurements, making it clear that also here the means for producing closure of the velum require the cooperation of the subject. Moreover, the nasal airways are isolated from the oral airways by the subject performing the Valsalva maneuver to consciously maintain a closed velum while a sample is aspirated through the nasal airways.

Another device is disclosed in CA 2 669 385, which shows a device for high flow therapy utilizing a non-sealing respiratory interface. This device concerns the delivery of therapeutic gases, mainly oxygen, and contains no mentioning of the possibility to close the soft palate. The device however comprises at least one sensor placed in or near the nares (the nostrils) in order to measure pressure, temperature or the concentration of oxygen. The disclosure however emphatically repeats that the nasal cannulas do not create a seal while the cannulas are in use.

U.S. Pat. No. 4,688,568 discloses a tube for ventilation, which simultaneously obturates (blocks) the esophagus. This tube has two inflatable cuffs, one that is placed in the pharynx, between the soft palate and the back of the tongue. There is however no mention of the measurement of NO, and the disclosure makes it clear that this is a device intended for emergency cases. Further, the disclosure is entirely silent on the possibility to regulate the airflow through the nasal airways, for example by opening and closing the pharyngeal cuff.

The cited exhaled-air collectors and devices are not suited for the determination of exhaled NO in infants and small children up to 6 years old, and also not suited for unconscious, demented or otherwise disabled adults, since these collectors either require an active cooperation of the patient, or fail to isolate the nasal airways, and are frequently uncomfortable to use. Thus, infants, small children or disabled adults are not capable of carrying out the necessary respiratory maneuvers independently and correctly.

Therefore, methods supplementing the ATS/ERS guidelines have been developed for infants and small children that can not cooperate. These methods are however all burdened with disadvantages.

At least one modified form of the "single-breath" method can be used with children older than 2 years old, in which method the regulation of flow takes place by an expiratory resistance that can be manually adjusted. The measuring of NO takes place online during normal spontaneous respiration.

However, as a rule in these methods, the maintaining of an exhalation parameter, usually the regulation of the flow, must be eliminated in order achieve at least the sufficient expiratory pressure in the buccal cavity. One way of guaranteeing the closure of the soft palate in a child, is for example that the child is allowed to blow into a balloon.

One particular problem associated with taking samples of exhaled air from infants and small children, is that they practically exclusively breathe in and out through the nose. Methods that make a permanent closure of the nose necessary can therefore not be used, as they would not be tolerated.

In order to prevent exhalation via the nose, one method prescribes shifting a face mask that covers the mouth and nose down during the exhalation so that the nose wings are compressed from the outside by the mask. The exhalation takes place into a collecting container. The entire apparatus comprises an expiratory resistance of 2 cm $H_2O$ that is slightly reduced in comparison to the ATS/ERS guidelines in order prevent a contamination by nasal NO.

Another "single-breath" method modified for infants operates with the artificial compression of the thorax and of the abdomen with the aid of a jacket that can be inflated and deflated with pressurized air, thereby exerting pressure on the thorax and abdomen. The passive exhalation takes place via a face mask against a resistance and at a constant expiratory flow of 50 ml/s. This method has a significant disadvantage in that the infants must be sedated during the procedure.

The invention therefore aims at making available devices and a system for collecting samples of exhaled air, for the purpose of diagnosing the lung function of uncooperative patients, such as infants and small children, and/or disabled, elderly and unconscious patients. The invention relates in particular to the determination of one or more component(-s) in exhaled air, for example, but not limited to nitric oxide (NO) in the exhaled air, aiming at making available a method with which the samples of exhaled air can be taken under normal respiratory conditions and in conformity with the ATS/ERS guidelines. When the component of exhaled air is nitric oxide (NO), contamination of the sample of exhaled air with nasal NO should be avoided to the extent possible.

SUMMARY

This objective is met by the features of the independent claims and advantageous embodiments are presented as the subject matter of the dependent claims, incorporated herein by reference.

One embodiment is an apparatus for the collection of samples of exhaled air during normal respiration, comprising a sample collector, an exhalation air receiver, and a device for isolating the nasal airways, wherein the apparatus further comprises:

- at least one sensor for detecting a change in a parameter representing the change from inhalation to exhalation and to transmit said change as a signal;
- a flow generator;
- a control unit, for example integrated in the flow generator, adapted to receive said signal and to control said device for isolating the nasal airways, and to control the flow generator creating a flow of exhaled air through the sample collector; and wherein
- the flow generator is in fluid communication with the sample collector; and the sample collector is in fluid communication with or integrated with the exhalation air receiver.

According to an embodiment, said exhalation air receiver comprises an elongated, hollow structure having a body for insertion into the oral cavity; with at least one inlet opening for exhalation air adapted to be positioned in the pharyngeal cavity, and an outlet opening adapted to be positioned outside the lips; wherein said at least one inlet opening communicates with the outlet opening via a hollow space of the body or via a tubing through the body, and the outlet opening is connected to the flow generator.

According to an embodiment, said exhalation air receiver comprises a mask, adapted to be placed over the mouth or the mouth and nose of a subject.

According to another embodiment, freely combinable with the above embodiments, the device for isolating the nasal airways comprises means for blocking the passage of air through the nasal airways, said means comprising inflatable pads adapted for placing on the outside of the nose between the root and the apex of the nose, which pads in inflated state compress the vestibule and/or atrium of both nostrils blocking the passage of air through the nasal airways.

According to another embodiment, the device for isolating the nasal airways comprises an orally insertable expandable body which, when in place in the oral cavity and positioned under the soft palate, in expanded state pushes the soft palate in a dorsocranial direction, preventing the passage of air between the nasal airways and the pharynx.

According to yet another embodiment, the device for isolating the nasal airways comprises means for blocking the passage of air through the nasal airways, said means comprising a pair of valves insertable in the nostrils.

Further, freely combinable with any of the above, said at least one sensor for detecting the inhalation and at least the beginning of the exhalation is chosen from an optical sensor, a temperature sensor, a flow meter, a pressure sensor, an impedance meter, an EEC electrode, a humidity sensor, an expansion meter, a piezoelectric sensor, an acoustic sensor, or any combination thereof.

According to an embodiment, freely combinable with any of the above, the flow generator comprises a gas-impermeable, flexible and inflatable collection bag surrounded by a container, which container can be evacuated, producing a vacuum in order to aspire a sample into said collection bag.

In the alternative, the flow generator comprises a pump or fan, adapted for accurately maintaining a flow in the range of 1-100 ml/s, preferably about 1 to about 50 ml/s, or preferably about 1-about 20 ml/s. It is conceived that the flow is adjusted to the volume and flow of exhaled breath of the patient or patient groups in question, applying a higher range to adults and a lower range to infants and children.

Another embodiment of the invention is an exhalation air receiver having an elongated, hollow structure with a body for insertion into the oral cavity, wherein said body has a flattened shape with an upward convex shape that conforms to the shape of the palate and a downward concave shape for receiving a section of the tongue.

Preferably said body for insertion into the oral cavity also comprises an expandable body which in expanded state pushes the soft palate in a dorsocranial direction, preventing the passage of air between the nasal airways and the pharynx.

Preferably said body for insertion into the oral cavity comprises a channel leading from a distal inlet opening for exhalation air that adapted to be positioned in the pharyngeal cavity, to a proximal outlet adapted to be positioned outside of the lips; and a channel leading from said expandable body to a connector positioned outside of the lips.

More preferably, said body for insertion into the oral cavity also comprises a channel allowing the measurement of the pressure in the pharynx and/or the oral cavity.

According to an embodiment, freely combinable with any one of the two previous embodiments mentioned herein, said channels in said exhalation air receiver have spacers on the inside of the channel walls, preferably in the form of nubs and/or ribs and/or webs that prevent said channels from being blocked by biting or exerting pressure on said insertable body when in place in the oral cavity.

According to another embodiment, freely combinable with any one of the two previous embodiments of the exhalation air receiver mentioned herein, said channels have longitudinal walls that prevent said channels from being blocked by biting or exerting pressure on said insertable body when in place in the oral cavity.

The exhalation air receiver preferably also comprises a moisture repellent filter or moisture absorbing means arranged in the channels or at the inlet openings into said channels of the exhalation air receiver, and in the channel or at the inlet or inlets into the pressure measuring line in order to prevent a closure by mucus and/or saliva.

Another embodiment is a device for isolating the nasal airways comprising means for blocking the passage of air through the nasal airways, wherein said means comprise inflatable pads adapted for placing on the outside of the nose between the root and the apex of the nose, which pads in inflated state compress the vestibule and/or atrium of both nostrils.

Preferably the above device further comprises at least one sensor for detecting the beginning of exhalation based on the detection of a change in a parameter measured in at least one nostril.

Preferably said at least one sensor is chosen from a flow sensor, a temperature sensor, a pressure sensor, a humidity sensor, or any combination thereof.

The invention also makes available a method of collecting samples of exhaled air during normal respiration conditions, comprising the steps of:
  detecting a change in a parameter representing the change from inhalation to exhalation and transmitting said change as a signal;
  receiving said signal in a control unit;
  activating a device for isolating the nasal airways;
  activating a flow generator connected to an exhalation air receiver; and
  collecting a sample of exhaled air during exhalation when the nasal airways are isolated.

According to a preferred embodiment, the method further comprises a step of deactivating the device for isolating the nasal airways when the end of an exhalation and/or the beginning of an inhalation is detected.

According to preferred embodiment, freely combinable with any of the methods disclosed herein, the detection of the inhalation and the beginning of the exhalation is based on the detection/measurement of one or more of oral pressure, flow of air in the airways, movements of the thorax and/or abdomen, electrical impulses as a sign of respiratory activity.

Further, according to an embodiment of the method, the device for isolating the nasal airways is activated when the beginning of exhalation is detected, or a preset period of time after the detection of the beginning of exhalation.

Preferably the aspiration of a sample of exhaled air takes place when the beginning of exhalation is detected, or when a preset period of time has elapsed from the detection of the beginning of exhalation.

Preferably, according to an embodiment of the method, the device for isolating the nasal airways is deactivated, and the aspiration of a sample of exhaled air interrupted, when a preset period of time has elapsed from the detection of the beginning of exhalation, or when the exhalation of a preset volume has been detected.

Preferably said preset time is determined on the basis of measured values for a normal respiration cycle, and similarly, a preset volume is determined on the basis of measured values for a normal respiration cycle.

Preferably, according to an embodiment of the method, the device for isolating the nasal airways is deactivated, and the aspiration of a sample of exhaled air interrupted when an inhalation phase of the next breathing cycle is detected.

According to an embodiment of the method, freely combinable with any other embodiment disclosed herein, the exhalation receiver is introduced orally and positioned with at least one inlet opening for exhalation air in the rear pharyngeal space.

Further, in a method according to any embodiment disclosed herein, a sample of exhalation air is collected during one or several breathing cycles.

Preferably the determination of a normal respiration cycle is based on the detection/measurement of one or more of oral pressure, flow of air in the airways, movements of the thorax and/or abdomen, and electrical impulses (impedance) as a sign of respiratory activity.

Preferably deviations from the normal respiration that indicate a premature inhalation bring about an interruption of the aspiration and a deactivation of the device for isolating the nasal airways.

According to one embodiment, freely combinable with any other embodiment disclosed herein, the beginning of the exhalation is detected by determining the $CO_2$ content of the exhaled air by a $CO_2$ analyzer to which the exhaled air is supplied.

According to another embodiment, freely combinable with any other embodiment disclosed herein, the sample of exhaled air is subjected to a qualitative or quantitative analysis of a component chosen from gaseous components such as carbon monoxide and nitric oxide; particulate matter such as for example cells, microbes, and macromolecules; and volatile organic compounds.

Preferably the sample of exhaled air is subjected to a quantitative analysis of the concentration of nitric oxide.

Most preferably the concentration of nitric oxide is determined in the sample of exhaled air, and wherein the parameters of the exhalation during which a sample is aspirated are controlled to values as set out in the ATS/ERS guidelines 2011.

BRIEF DESCRIPTION OF THE DRAWINGS

The embodiments of the invention will be described in closer detail with reference to the attached drawings, in which FIG. 1 schematically shows an embodiment of the invention comprising a sample collector 100, a receiver for exhaled air, here shown as an orally insertable receiver for exhaled air 200, a device 300 for isolating the nasal airways, a flow generator 400, at least one sensor 500, and a user interface 600.

FIG. 10 shows schematically (a) a longitudinal cross section of a double lumen mouthpiece 201 having longitudinal walls 230 stabilizing the shape of the mouthpiece, and forming two lumens 208 and 214; (b) a longitudinal cross section of a triple lumen mouthpiece 202, having three lumens 208, 214, and 215; and (c) a frontal cross section of a triple lumen mouthpiece 202, each according to embodiments of the invention.

DESCRIPTION OF PREFERRED EMBODIMENTS

In describing and claiming the embodiments of the invention, the following terminology will be used:

The singular forms "a", "an", and "the" include plural referents unless the context clearly dictates otherwise. Thus, for example, reference to "a sample" includes reference to one or more samples.

Also, the term "sample" is intended to include all types of samples obtainable from exhaled air, such as gaseous samples, liquid samples (exhaled breath condensate), particulate samples etc.

One embodiment is apparatus for the collection of samples of exhaled air during normal respiration, comprising a sample collector, an exhalation air receiver, and a device for isolating the nasal airways, wherein he apparatus further comprises:

a sensor for detecting a change in a parameter representing the change from inhalation to exhalation and to transmit said change as a signal;

a flow generator;

a control unit, for example integrated in the flow generator, adapted to receive said signal and to control said device for isolating the nasal airways, and to control the flow generator to create a flow of exhaled air through the sample collector; wherein the flow generator is in fluid communication with the sample collector; and the sample collector is in fluid communication with or integrated with the exhalation air receiver.

Figure 1:
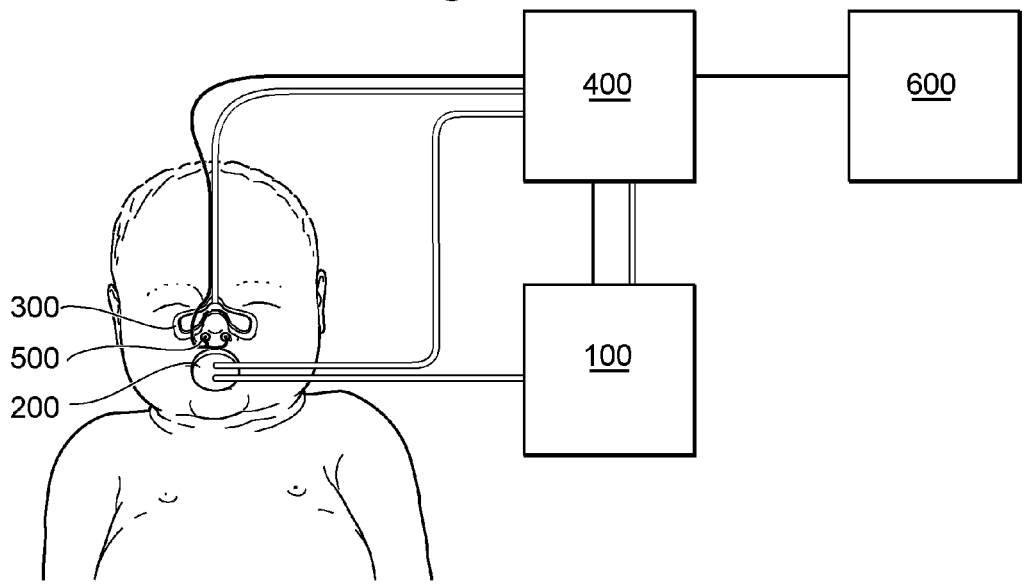

This is schematically shown in FIG. 1 where a flow generator is indicated as 400, connected to an orally insertable exhalation air receiver 200, and to a device for isolating the nasal airways 300, and in fluid connection with a sample collector 100. In the figure, also an interface 600 is indicated. Said interface can be a personal computer, a laptop, a hand-held computer or smart phone, or any device capable of displaying data and preferably also accepting operator input. A sensor (or sensors) 500 are also schematically shown, here indicated as placed near the nostrils of the patient.

As schematically shown in FIG. 1, the flow generator 400 is connected to the sensor 500, and adapted to receive a signal from said sensor. In the embodiment shown here, the flow generator 400 is also connected to the device for isolating the nasal airways 300, here indicated as an adhesive inflatable patch, and it is conceived that the flow generator pressurizes said patch with a fluid, such as air, water or an inert gas, in order to close the nasal airways.

The connection between the sample collector 100 and the orally insertable exhalation air receiver 200 is shown as a tube, as well as the connection between the sample collector and the flow generator 400, indicating that the flow generator is capable of aspirating a sample from the exhalation air receiver, via the sample collector. The second tube, connecting the flow generator and the exhalation air receiver indicates that the flow generator also has the capability of independently measuring the pressure in the oral cavity, and/or to control a device for isolating the nasal airways (not shown) incorporated in the orally insertable exhalation air receiver 200.

Figure 2:
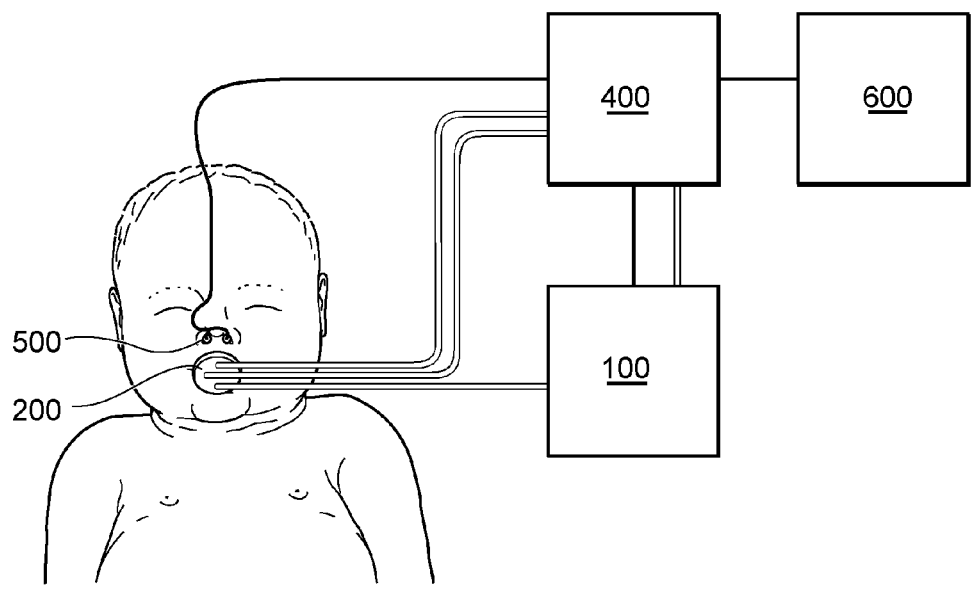
FIG. 2 schematically shows another embodiment, where the device 300 for isolating the nasal airways is integrated in an orally insertable receiver for exhaled air 200, and controlled by the flow generator 400.

FIG. 2 schematically shows another embodiment, where the device 300 for isolating the nasal airways is integrated in an orally insertable receiver for exhaled air 200, and controlled by the flow generator 400. Thus, there is no external means for isolating the nasal airways. The sensors 500 are however indicated in the figure, as well as two tubes connecting the exhalation gas receiver 200 and the flow generator 400, indicating that the flow generator is adapted to both measure the pressure in the oral cavity, and to operate the device for isolating the nasal airways (not shown) incorporated in the orally insertable exhalation air receiver 200.

Figure 3:
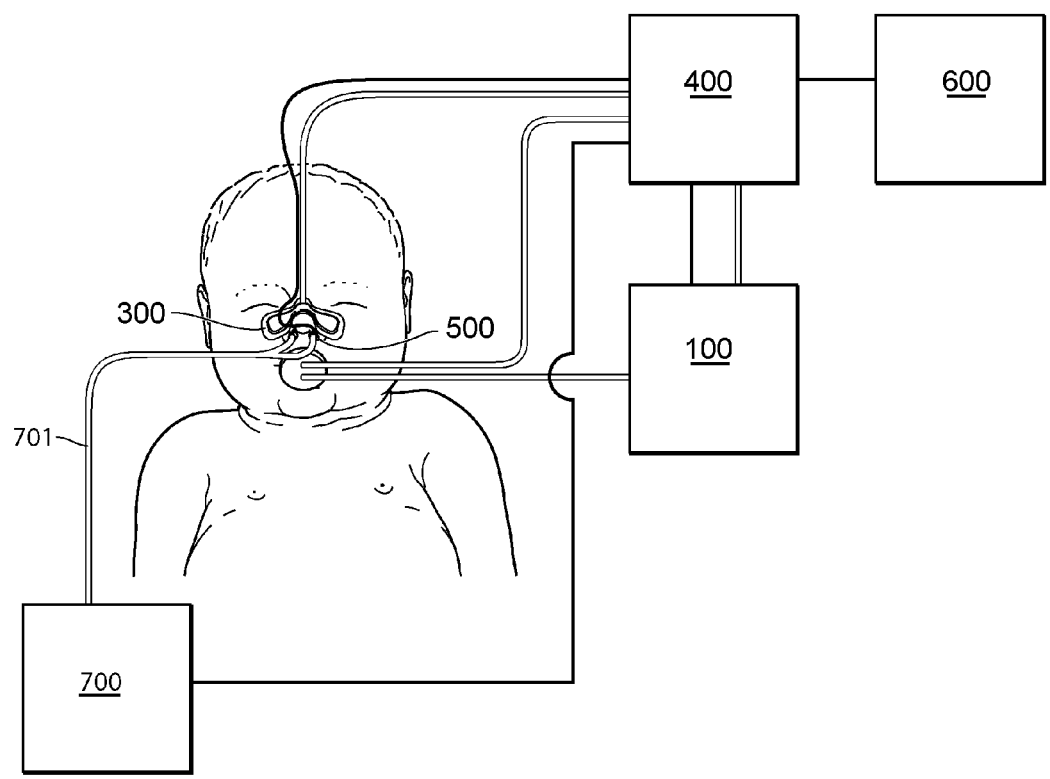
FIG. 3 schematically shows another embodiment, freely combinable with the above embodiments, further comprising a unit 700 for delivering a gas to the subject, including flexible tubing 701.

FIG. 3 shows another embodiment, where the flow generator 400 is connected to and capable of controlling a unit 700 for administering inhalation gas to the patient, for example through flexible tubing 701 ending in nasal cannulas, soft plastic tube ends fitting into the nostrils or close to the same. The inhalation gas is preferably of a well known composition, and most preferably does not contain the component or components that are to be detected in the sample of exhaled air obtained with the device and method according to embodiments of the invention. When the component to be detected is NO, the inhalation gas is preferably NO-free gas. This can be achieved by incorporating a pump or fan, and a NO-scrubber into unit 700, thus drawing ambient air through the NO-scrubber before delivering it to the patient.

Figure 4:
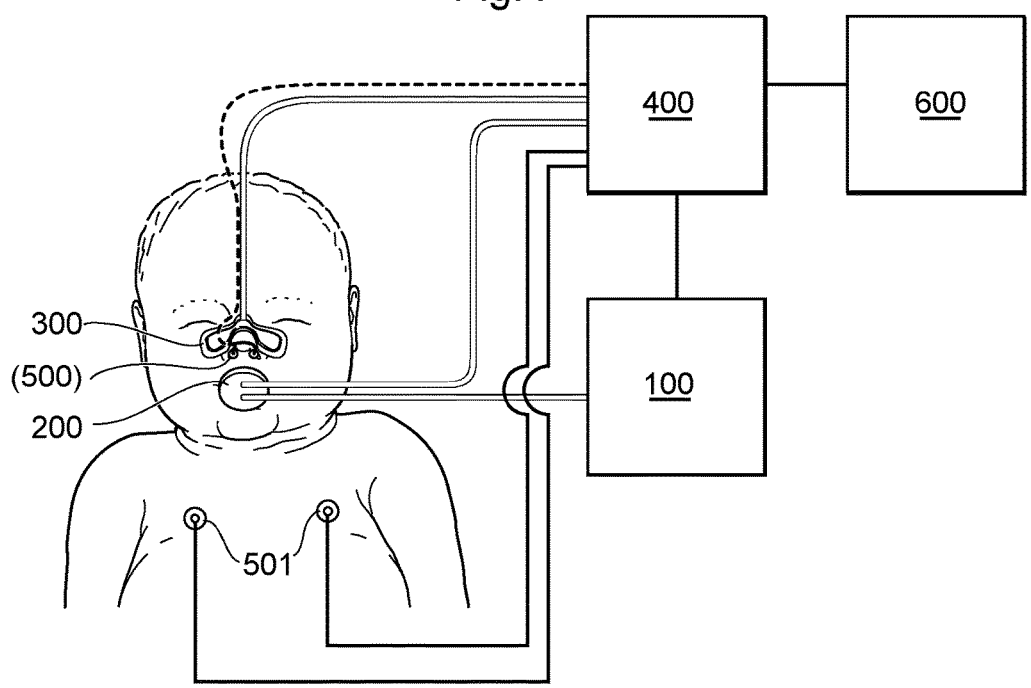
FIG. 4 schematically shows an embodiment freely combinable with the above embodiments, where a flow generator 400 includes means to detect the breathing pattern based for example on impedance measurement, using at least one sensor 501 placed on the chest of the subject. The use of a sensor or sensors 501 placed on the chest makes the use of sensors 500 placed at the nostrils of the patient optional, wherefore these are indicated with a dashed line and the reference number placed in parenthesis.

FIG. 4 shows another embodiment, where the flow generator 400 is connected to one or more sensors 501, attached to the chest of the patient, capable of detecting electrical impulses of the body, indicative of the different phases of the respiratory cycle, such as inhalation, exhalation, breath hold etc. Suitable electrodes are commercially available and easily accessible to a skilled person, for example electrodes for impedance measurements. The sensors 501 may supplement or replace other sensors, such as the sensor or sensors 500 situated in or near the nostrils. For this reason, the connection between the sensor 500 and the flow generator 400 is indicated by a dashed line.

As infants or small children do not tolerate the active closing of the nose by the nose closure means or a flow through meter inserted into the nostril, the breathing movement of the child, that is the raising and lowering of the thorax and/or of the abdomen, can be used for the recording, in particular for the detection of a beginning of an inhalation phase and/or an exhalation phase of a breathing cycle. This can be relied on in addition to, or as an alternative to other techniques described herein. Such measuring- and data detection devices are known from the state of the art. For example, such a medical product can be a breast belt with integrated expansion strips.

Figure 5:
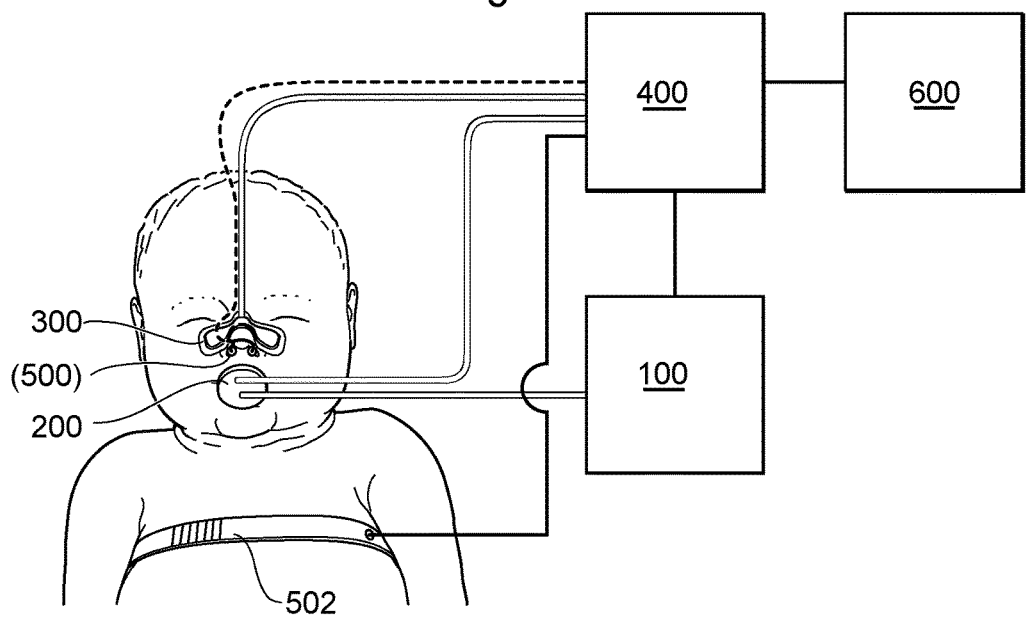
FIG. 5 schematically shows another embodiment freely combinable with the above embodiments, where a flow generator 400 includes means to detect the breathing pattern for example based on the detection of chest movement or the expansion of the chest and/or abdomen using one or more sensor(-s) 502 placed on the chest of the subject. Also here, the use of sensors 502 placed on the chest/abdomen makes the use of sensors 500 placed at the nostrils of the patient optional, wherefore these are indicated with a dashed line and the reference number placed in parenthesis.

Accordingly, FIG. 5 shows such an embodiment, where the flow generator 400 is connected to one or more sensors 502, attached to the chest of the patient, capable of detecting movement, for example expansion and contraction of the chest or abdomen, indicative of the different phases of the respiratory cycle. The sensors 502 may supplement or replace other sensors, such as the sensor(-s) 500 situated in or near the nostrils. For this reason, the connection between the sensor 500 and the control unit 400 is also here indicated by a dashed line.

Figure 6:
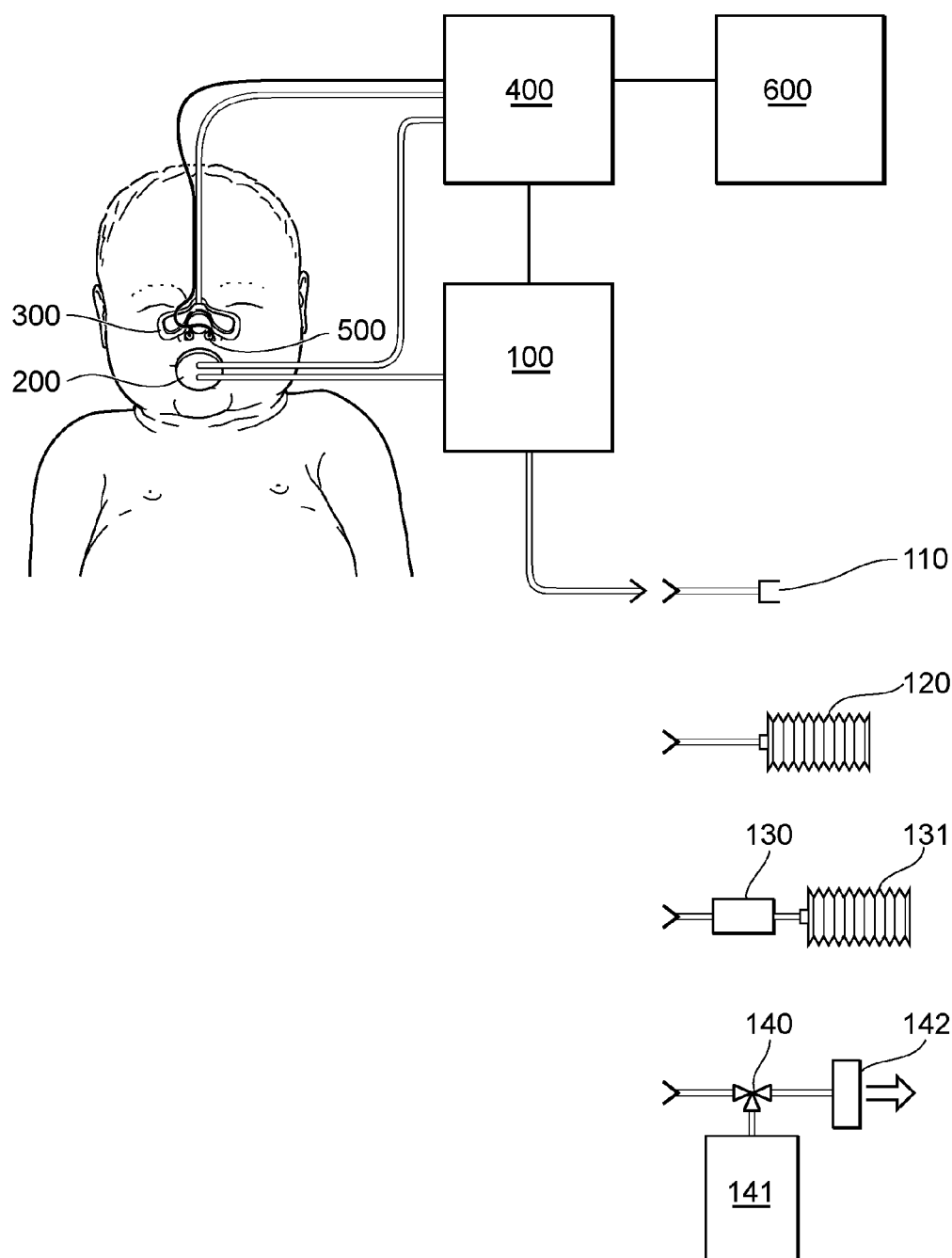
FIG. 6 schematically shows how any of the embodiments can further comprise a connection or a manifold, adapted to lead a sample to different means (for example a port 110, a sample bag 120, a filter/scrubber 130 and a sample bag 131, a valve or valves 140, a source of calibration gas 141, and a filter 142) for further storage, processing or analysis of the sampled exhalation air.

FIG. 6 shows an embodiment, similar to that shown in FIG. 1 and freely combinable with any other embodiment disclosed herein, where the sample collector 100 supplies a sample of exhaled air to a port 110 for connection to any auxiliary apparatus, for example an apparatus for analyzing the presence and/or concentration of a component of the exhaled air. The sample collector can include a manifold with one or more such ports, and the sample can be led into an expandable sample bag 120 or 131, for example a MYLAR® bag, either directly, or via a filter or scrubber 130, for example a moisture filter and/or a $CO_2$ scrubber. The sample collector may also be connected via suitable valves 140 to a source of calibration gas 141, and the outlet may also comprise a flow resistance 142.

According to an embodiment, the exhalation air receiver comprises an elongated, hollow structure having a body for insertion into the oral cavity; with at least one inlet opening for exhalation air adapted to be positioned in the pharyngeal cavity, and an outlet opening adapted to be positioned outside the lips; wherein said at least one inlet opening communicates with the outlet opening via a hollow space of the body or via a tubing through the body, and the outlet opening is connected to the flow generator.

Preferably the exhalation air receiver is designed like a pacifier, with a pacifier body that is at least partially hollow. It comprises at least one inlet opening for the exhaled air that is adapted to be positioned in the pharyngeal cavity. An outlet opening outside of the mouth is arranged on the mouth outlet side, whereby the at least one inlet opening communicates with the outlet opening via at least one hollow space of the pacifier body or via flexible tubing, a conduit or channel through the pacifier body.

Additionally, the pacifier form or teat form has the advantage that infants and small children rapidly and easily accept this as a rule. In addition, this has a calming effect on the child, since it makes sucking possible, as in the case of a commercial pacifier.

According to another embodiment, freely combinable with the other embodiments mentioned herein, a pressure measuring line can be run through the exhalation air receiver. The pressure measuring line, preferably corresponding with a pressure sensor, placed in the exhalation air receiver, or more preferably placed in the flow generator or in the control unit, serves to determine the inner pressure in the buccal cavity and/or in the pharyngeal space. During the change of the breathing cycle from inhalation to exhalation the pressure in the mouth space/pharyngeal space rises slightly. These pressure differences can be detected, and used to indicate the beginning of exhalation. Then, a signal can be generated by the control unit in accordance with the determined pressure data, which signal preferably activates and/or deactivates the velum closure means and/or the nose closure means.

A moisture-repellent filter or moisture-absorbing means can be arranged on or in the inlet opening or the inlet openings into the exhalation air receiver and on or in the inlet into the pressure measuring line in order to prevent a closure by mucus and/or saliva. This ensures that the taking of the sample as well as the detection of the measuring data in the oral cavity do not have to be interrupted in order to clean or replace the exhalation air receiver.

According to another embodiment, the device for isolating the nasal airways comprises an orally insertable expandable body which, when in place in the oral cavity and positioned under the soft palate, in expanded state pushes the soft palate in a dorsocranial direction, preventing the passage of air between the nasal airways and the pharynx.

Further, freely combinable with any of the above, said at least one sensor for detecting the inhalation and at least the beginning of the exhalation is chosen from an optical sensor, a temperature sensor, a flow meter, a pressure sensor, an impedance meter, an EEC electrode, a humidity sensor, an expansion meter, a piezoelectric sensor, an acoustic sensor, or any combination thereof.

According to an embodiment, freely combinable with any of the above, the flow generator comprises a gas-impermeable, flexible and inflatable collection bag surrounded by a container, which container can be evacuated, producing a vacuum in order to aspire a sample into said collection bag.

In the alternative, the flow generator comprises a pump or fan, adapted for accurately maintaining a flow in the range of 1-100 ml/s, preferably about 1 to about 50 ml/s, or preferably about 1-about 20 ml/s. It is conceived that the flow is adjusted to the volume and flow of exhaled breath of the patient or patient groups in question, applying a higher range to adults and a lower range to infants and children.

Another embodiment of the invention is an orally insertable exhalation air receiver having an elongated, hollow structure with a body for insertion into the oral cavity, wherein said body has a flattened shape with an upward convex shape that conforms to the shape of the palate and a downward concave shape for receiving a section of the tongue.

Preferably said body for insertion into the oral cavity also comprises an expandable body which in expanded state pushes the soft palate in a dorsocranial direction, preventing the passage of air between the nasal airways and the pharynx.

In this context, velum closure means that the soft palate (velum) is pressed upward and as a result the nasopharynx is isolated in order to avoid contaminations of the exhaled air with nasal NO. The velum closure can preferably be switched back and forth between at least two positions and/or shapes corresponding to two states, e.g. "deactivated" and "activated" or "open" and "closed" with reference to its effect on the velum. In a first position or first state, there is no contact with the velum of the patient. The velum can then move freely. In a second position or a second state, there is contact between the closure means and the velum of the patient, as result of which the velum is pressed against the back pharyngeal space. In this position the velum can no longer freely move and at the same time closes the nasopharynx. The velum closure means is activated in particular at the start of exhalation, as a result of which it actively guides the velum against the back pharyngeal space.

The velum closure means is preferably a deformable swelling body, whereby the shape and extent of the deformation of the swelling body can be controlled by the control unit, whereby the shape and extent of the deformation results in the closure of the velum. The swelling body can be an expandable body that is filled with a non-compressible medium, preferably with water. Alternatively or additionally the swelling body can be expanded by the supplying of compressed air. The casing of the swelling body can comprise areas of different expandability, as a result of which the shaping of the deformation can be given by the shaping of the casing, since a casing area with a greater expandability expands more strongly than a casing area with a greater rigidity.

According to a particular embodiment, the swelling body is a component of the orally insertable exhalation air receiver or pacifier body. The swelling body integrated in the pacifier body is preferably a hollow space arranged in the pacifier body which hollow space can be deformed by compressed air. The supply and removal of the compressed aid into/from the swelling body is controlled by the control apparatus, preferably in accordance with the determined progress data of one or more breathing cycles. The compressed air can preferably be supplied to and removed from the swelling body through a line, whereby the line is run through the pacifier body and can be alternately connected to a compressed-air container or to an outlet.

Preferably said body for insertion into the oral cavity comprises a channel leading from a distal inlet opening for exhalation air that adapted to be positioned in the pharyngeal cavity, to a proximal outlet adapted to be positioned outside of the lips; and a channel leading from said expandable body to a connector positioned outside of the lips.

More preferably, said body for insertion into the oral cavity also comprises a channel allowing the measurement of the pressure in the pharynx and/or the oral cavity.

According to an embodiment, freely combinable with any one of the two previous embodiments mentioned herein, said channels in said air receiver have spacers on the inside of the channel walls, preferably in the form of nubs and/or ribs and/or webs that prevent said channels from being blocked by biting or exerting pressure on said insertable body when in place in the oral cavity. This would prevent the collection process as well as the function of the exhalation air receiver from being interrupted by spontaneous movements of the mouth or jaw, suction, or the tongue of the child. To this end the spacers preferably have perforations and/or are offset in such a manner that passage of the gases and fluids to be transported through the exhalation air receiver is always ensured.

The exhalation air receiver preferably also has a moisture repellent filter or moisture absorbing means arranged on or in the inlet openings into the exhalation air receiver, and on or in the inlet or inlets into the pressure measuring line, in order to prevent the channels from becoming blocked by mucus and/or saliva.

Figure 7:
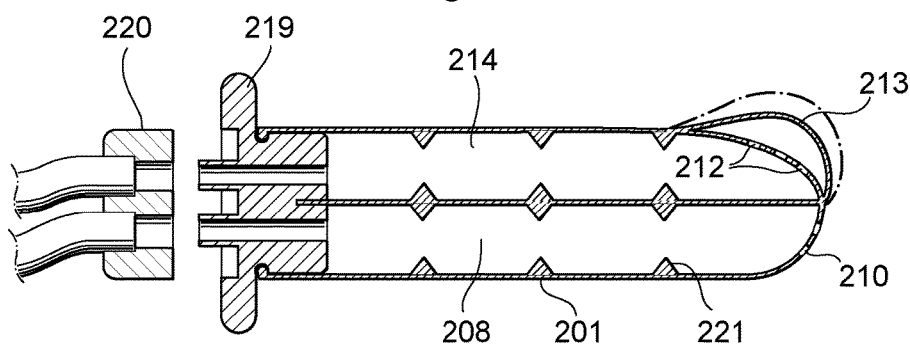
FIG. 7 schematically shows a longitudinal cross section view of an orally insertable receiver 200 for exhaled air in the shape of a double lumen mouthpiece 201 with an optional expandable portion 213.
Figure 8:
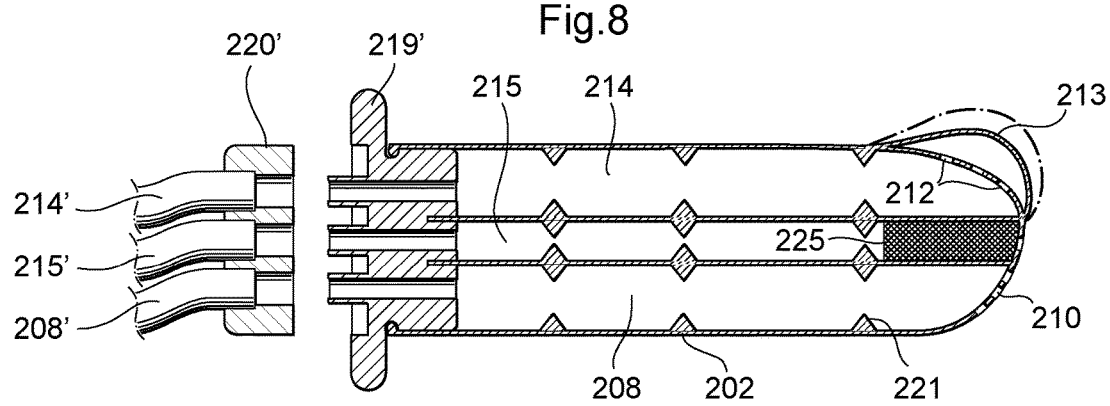
FIG. 8 schematically shows a longitudinal cross section view of an orally insertable receiver 200 for exhaled air in the shape of a triple lumen mouthpiece 202 with an optional expandable portion 213.
Figure 9A:
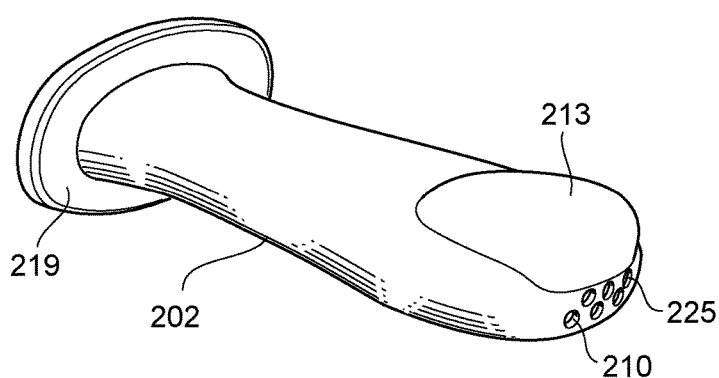
FIG. 9 shows a side view (a) and a frontal view (b) of an orally insertable receiver 200 for exhaled air according to an embodiment of the invention, here shown as a triple lumen mouthpiece 202 from FIG. 8.
Figure 9B:
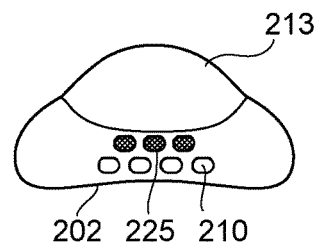

An orally insertable exhalation air receiver 200 is schematically shown in FIGS. 7, 8, and 9. A double lumen exhalation air receiver 201 according to an embodiment of the invention is schematically shown in cross section in FIG. 7, where a first channel 208 communicates with an opening 210, and another channel 214 communicates with an expandable body 213. Both channels preferably have internal nubs 221 that prevent said channels from being blocked when the air receiver is compressed by the patient, e.g. by biting on it. The insertable exhalation air receiver preferably terminates in a plug 219, facilitating the connection between the air receiver and the flow generator and/or control unit. It is conceived that the insertable exhalation air receiver is a single-use item, only used for one patient and then discarded. To facilitate the connection, the plug 219 fits into a socket 220. In the alternative, the channels 214 and 208 continue as flexible tubing outside the insertable exhalation air receiver, and this tubing is then connected to the flow generator and/or control unit (not shown).

FIG. 8 shows another embodiment of an insertable exhalation air receiver 200, here shown as triple lumen exhalation air receiver 202, having a first channel 208 communicating with an opening 210, another channel 214 communicating with an expandable body 213, and a third channel 215 communicating with a pressure sensor (not shown) and terminating in an opening having a filter and/or saliva trap 225. In the figure, all three channels are shown with internal nubs 221. Further, as in the above embodiment, it is conceived that the insertable triple lumen exhalation air receiver 202 terminates in a plug 219' that fits a corresponding socket 220' with the exception that here, said plug and socket accommodate connections for three channels, 208', 214' and 215'. In the alternative, the channels 208, 214, and 215 continue as flexible tubing outside the insertable exhalation air receiver, and this tubing is then connected to the flow generator and/or control unit (not shown).

FIG. 9 then shows a perspective view of an insertable exhalation air receiver 200 according to an embodiment, a triple lumen exhalation air receiver 202 as shown in FIG. 8. Here, the anatomical form of the air receiver is indicated at least schematically, as well as the position of the expandable body 213 and the opening or openings 210 and 225.

FIG. 10 shows schematically in (a) a longitudinal cross section of a double lumen mouthpiece 201 having longitudinal walls 230 stabilizing the shape of the mouthpiece, and forming two channels, 208 and 214; and in (b) a longitudinal cross section a triple lumen mouthpiece 202, having three channels, 208, 214, and 215; and in (c) a frontal cross section of a triple lumen mouthpiece, each according to embodiments of the invention.

In FIGS. 10 a, b and c, position 208 indicates a first channel communicating with an opening 210, having a saliva trap in the form of fibrous material or a filter 225; another channel 214 communicating with an expandable body 213 via an opening 212. FIGS. 10 b and c, also show a third channel 215 having an opening into the pharynx, and communicating with a pressure sensor (not shown). Preferably said channel also has a saliva trap or filter 225, similarly as in channel 208.

As shown in FIG. 10, the channels are separated by longitudinal walls 230 that prevent said channels from being blocked by biting or exerting pressure on said insertable body when in place in the oral cavity.

In FIG. 10, also the plug 219 and 219' are shown, indicating both their function as a connector to tubes or to a socket, and their function as a stop, preventing the body from being inserted too far into the mouth, or from being inadvertently swallowed etc.

Another embodiment is a device for isolating the nasal airways comprising means for blocking the passage of air through the nasal airways, wherein said means comprise inflatable pads adapted for placing on the outside of the nose between the root and the apex of the nose, which pads in inflated state compress the vestibule and/or atrium of both nostrils.

Preferably the above device further comprises at least one sensor for detecting the beginning of exhalation based on the detection of a change in a parameter measured in at least one nostril.

Preferably said at least one sensor is chosen from an optical sensor, a flow sensor, a temperature sensor, a pressure sensor, a humidity sensor, or any combination thereof.

According to another embodiment, freely combinable with the above embodiments, the device for isolating the nasal airways comprises a means for blocking the passage of air through the nasal airways, said means comprising inflatable pads adapted for placing on the outside of the nose between the root and the apex of the nose, which pads in inflated state compress the vestibule and/or atrium of both nostrils blocking the passage of air through the nasal airways.

In a preferred embodiment this is an adhesive and inflatable patch, plaster or bandage that covers the wings of the nose, preferably with a least one chamber that can be inflated with a fluid, for example water or air, whereby the inflating and deflating is initiated and controlled by the control unit. In the case that air is used, the required inflating air can preferably be made available via a supply line from a compressed-air container.

The nose plaster preferably consists of two hollow chambers that are each placed on a wing of the nose. In a special embodiment the plaster consists of two layers that can be expanded with different strengths and between which a hollow space or the chambers is/are arranged. The upper cover layer of the plaster is preferably manufactured from a material with lesser expandability than the lower layer resting on the skin. This brings it about that during the inflation of the hollow space or of the chambers with compressed air the lower layer expands more strongly and presses against the wings of the nose, which achieves a closure of the nose.

Figure 14A:
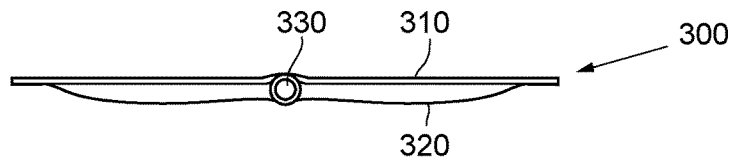
FIG. 14 schematically shows a device for isolating the nasal airways in the shape of a double walled adhesive patch, (a) in inactive (resting); and (b) in active (inflated) state; and (c) a frontal, partial cut-out view of the same.
Figure 14B:
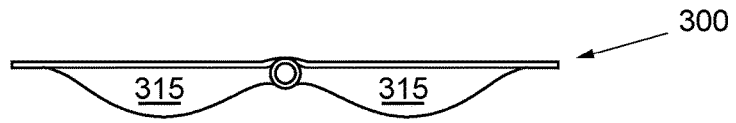
Figure 14C:
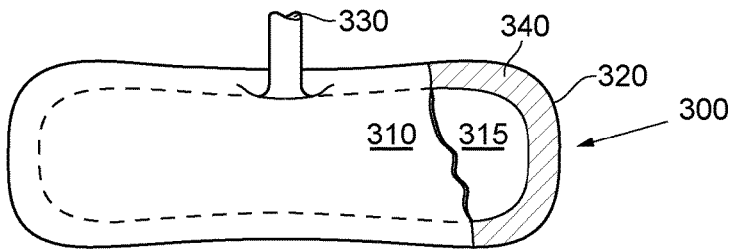
Figure 15A:
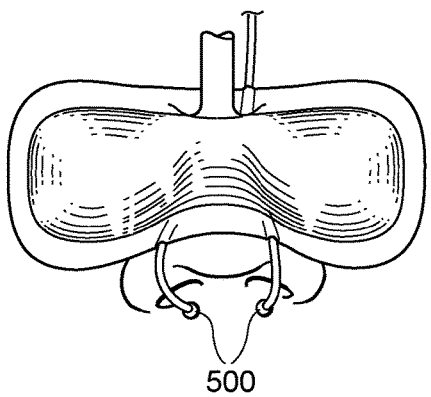
FIG. 15 shows schematically two perspective views of an embodiment of the double walled adhesive patch 300 in use, one from the front (a), and one from the side (b), also including at least one optional sensor 500 for detecting a parameter of the nasally exhaled air, optionally held in place by the adhesive patch 300.
Figure 15B:
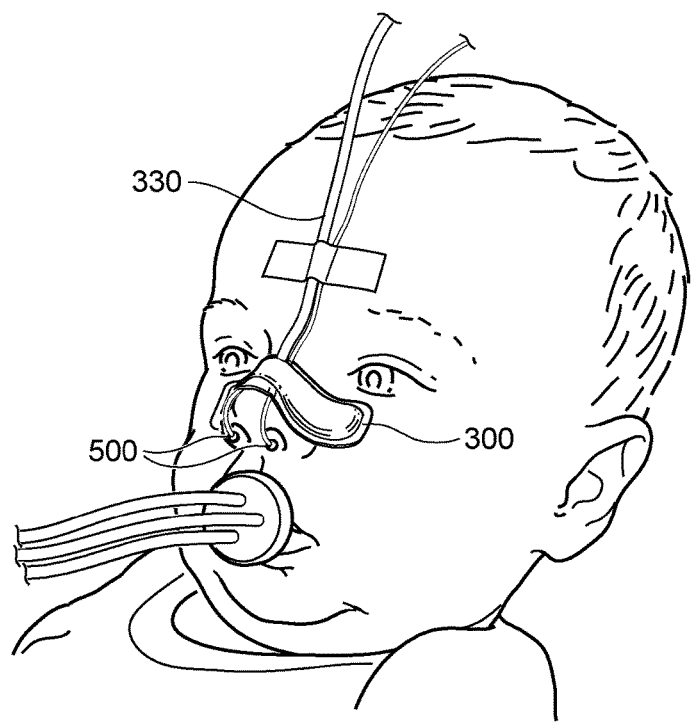

One example of this embodiment is schematically shown in FIGS. 14 and 15, where panel a) shows a cross section of an inflatable patch 300, comprising a first layer 310 and a second layer 320, attached to each other along the periphery of the patch, forming a hollow space between the layers. A flexible tubing in fluid communication with said hollow space is shown as 330. In panel b) the patch has been inflated by feeding a fluid, for example air or water, through the tubing 330 into the space 315. As disclosed above, the upper layer is preferably thicker and/or stronger and thus less flexible, and the lower layer thinner and more elastic, thus guiding the expansion towards the wings of the nose. The lower layer can for example be made of polyurethane film, silicone or similar material, suitable for contact with the skin.

Panel c) shows a partial cut-out view of the patch, showing the upper layer 310, the lower layer 320, and the hollow space 315. The dashed area 340 indicates the seal between the upper and lower layers, formed for example by melting or gluing the layers.

FIG. 15 shows the patch 300 in use, placed over the nose of a patient, indicating that the flexible tubing 330 can be led over the forehead of the patient. Panels a) and b) both indicate that the patch 300 can either comprise or be used simultaneously with one or more sensors 500, placed near the nostrils to detect a change in a parameter of exhaled air, such as the flow, temperature, humidity, or CO2 concentration, in order to detect the breathing rhythm and/or the beginning of an exhalation. The sensor or sensors 500 are preferably separate, but can be held in place by the adhesive patch 300.

According to yet another embodiment, the device for isolating the nasal airways comprises means for blocking the passage of air through the nasal airways, said means comprising a pair of valves insertable in the nostrils.

Figure 11:
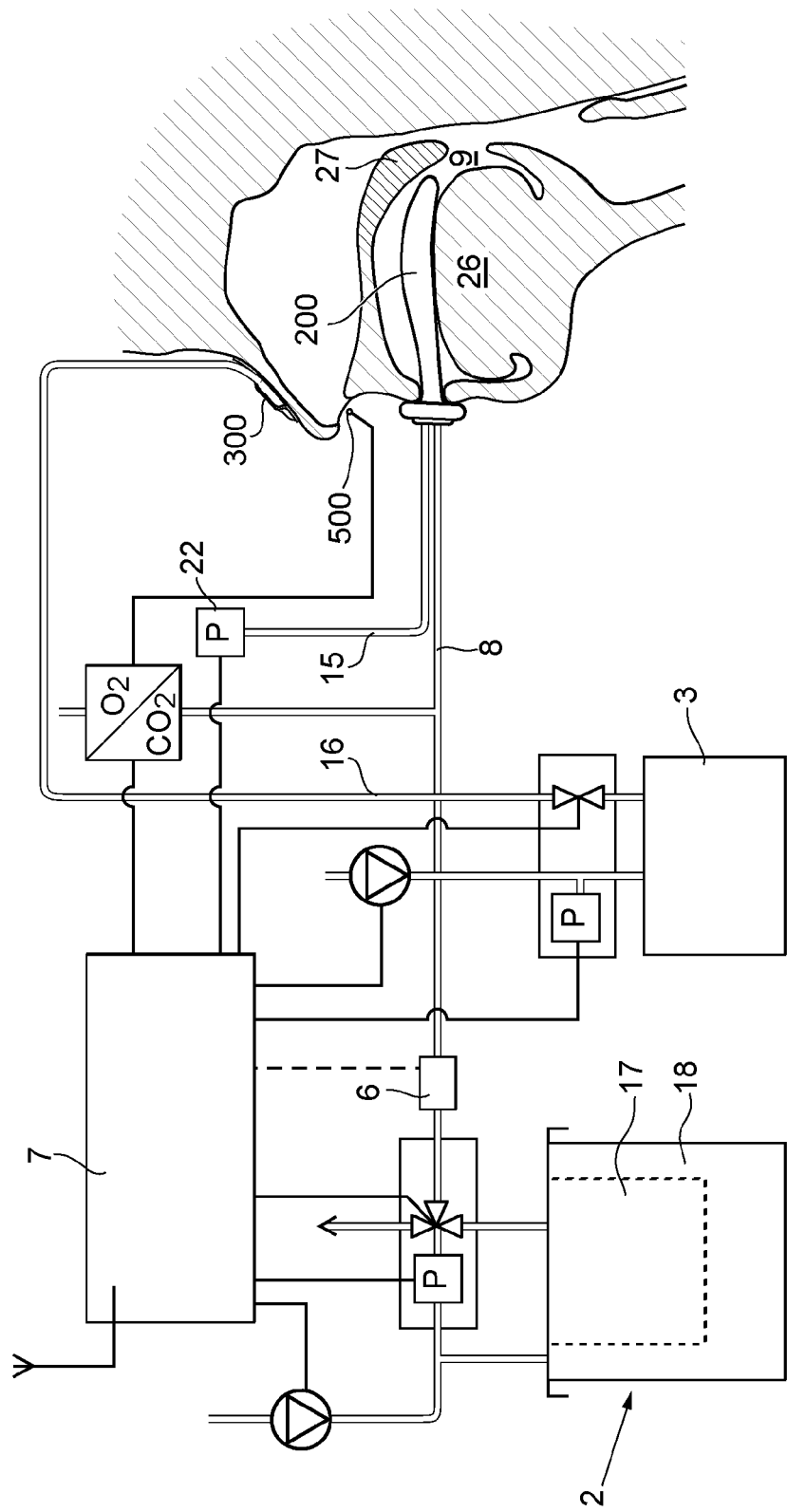
FIG. 11 schematically shows an embodiment where the flow generator and sample collector operate according to the "bag-in-box" principle, an orally insertable receiver for exhaled air 200 is used, and where the means for closing the nose comprise an adhesive, expandable nose closing device 300.

FIG. 11 shows an apparatus for the collection of samples of exhaled air under normal respiration conditions according to an embodiment where an orally insertable exhalation air receiver 200 is used together with device 300 for isolating the nasal airways. Additionally, sensors 500 are in place in the nostrils. The exhalation air receiver 200 is inserted orally and extends into the buccal cavity or oral pharyngeal cavity 9 and lies between the pallet and tongue 26.

Figure 12:
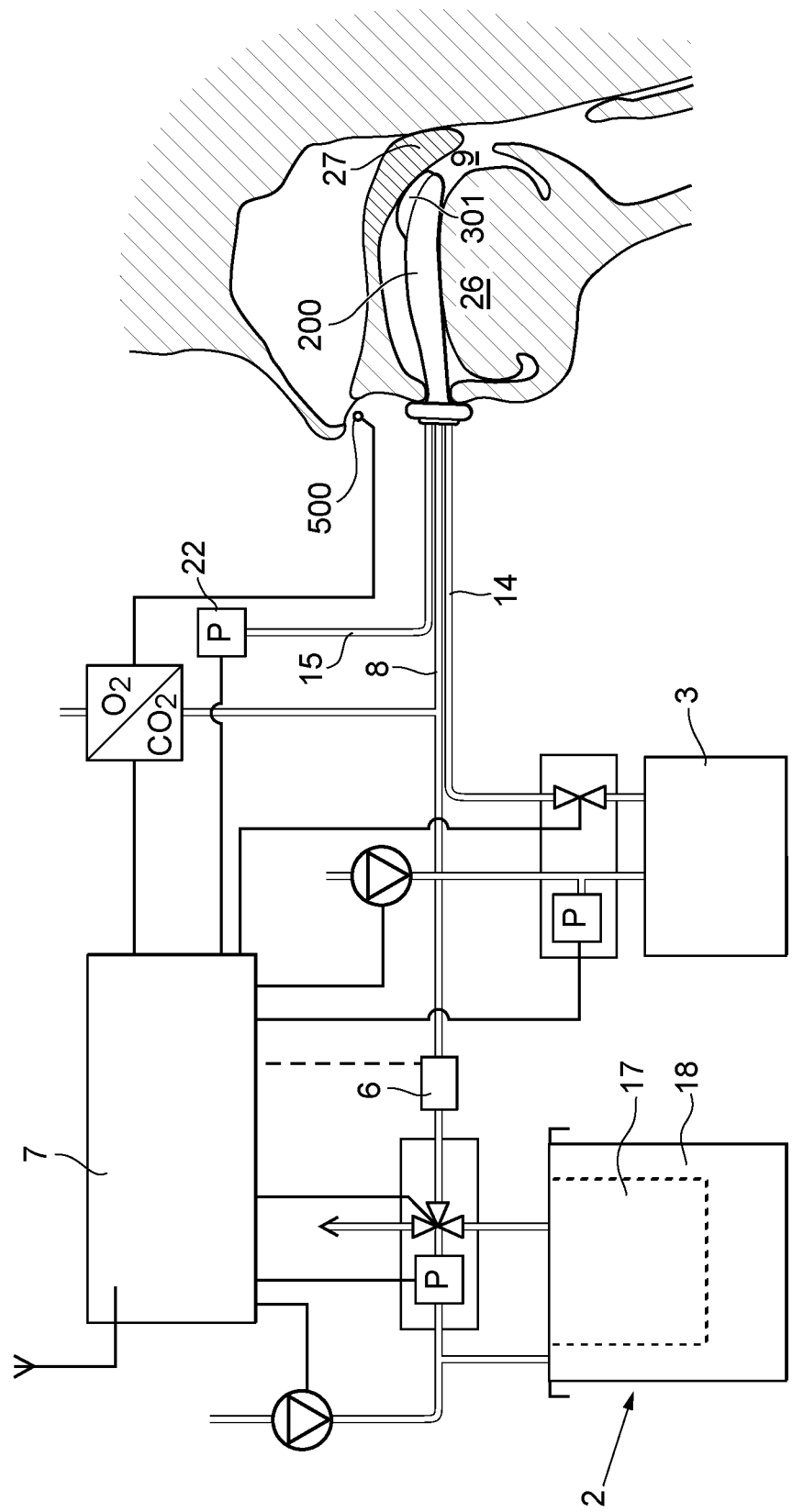
FIG. 12 schematically shows an embodiment where the flow generator and sample collector operate according to the "bag-in-box" principle, and where the means for closing the nose comprise an expandable element adapted for positioning in the oral cavity, here shown as an expandable element 301 integrated in the orally insertable receiver for exhaled air.
Figure 12A:
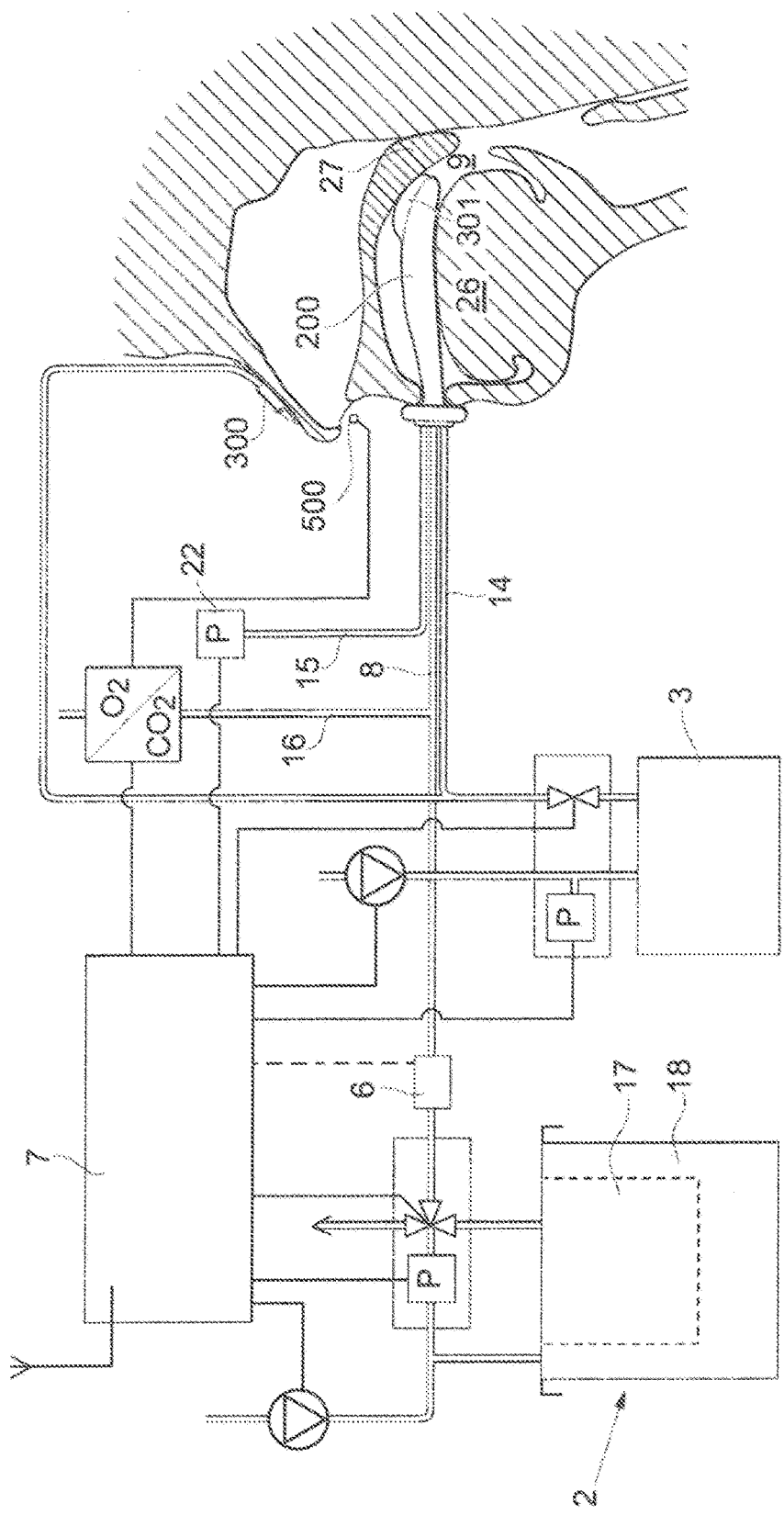
FIG. 12A schematically shows an embodiment where the flow generator and sample collector operate according to the "bag-in-box" principle.

The exhalation air receiver 200 may be equipped with a velum closure means in the form of an expandable body 301, for the purpose of temporarily closing the velum 27 (e.g., as shown in FIG. 12A). It is however conceived that the device 300 for isolating the nasal airways will be sufficient.

The exhalation air receiver 200 is connected via a pressure measuring line 15 to a pressure sensor 22, with which the pressure in the buccal cavity is detected in order to determine the beginning and end of the exhalation phase and/or of the inhalation phase.

A nose closure means 300 is placed on the patient's nose and communicates via line 16 with a compressed air container 3. Valves and a pressure sensor are merely indicated for illustration purposes. The nose closure means 300 is an inflatable adhesive patch which covers the nose wings and is filled via line 16 with compressed air from the compressed air container 3. The inflating and deflating of the patch is initiated by the control unit 7 and can be controlled and regulated by it. In inflated state, the patch closes the patient's nose, so that he can no longer exhale through it. The apparatus further comprises a flow generator having a collection container 2 for exhalation air which communicates with the exhalation air receiver 1 via a hose line or tubing 8. A suction pressure for the removal of the exhalation air can be established and adjusted in the collection container 2.

According to one embodiment, the collection container 2 consists of a gas-impermeable, flexible collection bag 17 into which the exhaled air is drawn by suction. The collection bag 17 is surrounded by a rigid container 18. The container 18 is evacuated in order to establish a suction pressure, which generates a vacuum in the container 18. The degree of the evacuation for generating a defined vacuum is adjusted and controlled by the control unit 7. By applying a vacuum in the surroundings of the collection container 17 the collection container 17 draws in the exhaled air and stores it at the same time. A flow regulator or flow meter 6 is arranged in line 8, using which the required exhalation current is adjusted. The flow regulator 6 can be a passive or an active flow regulator, and in the case of an active flow regulator, the control unit 7 controls the flow regulator as indicated by the dashed line between these two components.

FIG. 12 shows an alternative embodiment without nose closure means. The exhalation air receiver 200 is again inserted orally and extends into the focal cavity or the pharyngeal cavity 9 and lies between pallet and tongue 26. The exhalation air receiver 200 is equipped with a velum closure means arranged for the temporary closure of the velum 27. The velum closure means comprise a swelling body 301. The shape of the deformation of the swelling body can be controlled by the control unit 400, whereby an expansion of the swelling body leads to a closure of the velum 27. The swelling body 301 is filled with an incompressible medium and is filled via the pressure line 14 with compressed air from the pressure container 3 for the purpose of expanding the swelling body 13.

The apparatus also comprise a flow generator having a collection container 2 for exhalation air that communicates with the exhalation air receiver 200 via a hose line 8. A suction pressure for the removal of the exhalation air can be established and adjusted in the collection container 2.

The collection container 2 consists of a gas-impermeable, flexible collection bag 17 into which the exhaled air is drawn in by suction. The collection bag 17 is surrounded by a rigid container 18. The container 18 is evacuated in order to establish a suction pressure, which generates a vacuum in the container 18. The degree of the evacuation for generating a defined vacuum is adjusted and controlled by the control unit 7. By applying a vacuum in the surroundings of the collection container 17 the collection container 17 draws in the exhaled air and stores it at the same time. A flow regulator 6 is arranged in line 8, using which the required exhalation flow is adjusted. As disclosed in the context of FIG. 11 above, the flow regulator 6 can be a passive or an active flow regulator, and in the case of an active flow regulator, the control unit 7 controls the flow regulator as indicated by the dashed line between these two components.

The hose line between the exhalation air receiver and the collection container can comprise a throttle apparatus and/or a flow regulator, e.g., an appropriately constructed PEEP valve.

It is preferred that the collection container comprises a gas-impermeable, flexible collection bag that can be filled with the exhaled air and is surrounded by a container. The container can be evacuated in order to produce a suction pressure, as a result of which a vacuum is produced in the container. The degree of the evacuation for producing a defined vacuum can preferably be adjusted and controlled by the control apparatus, thus controlling the sample flow. The collection bag draws the exhaled air in by applying a vacuum in the surroundings of the collection bag and stores it at the same time.

For the detachable connection of the outlets and inlets of the exhalation air receiver on the outside of the mouth, in particular of the pacifier body, to the supply lines and discharge lines of the apparatus the latter can be constructed on both sides as plug connections, preferably combined in a plug and a socket. In a preferred embodiment the socket body and/or plug body can be moved further into the exhalation air receiver, in particular into the pacifier body, at least into an area that is located in the orally inserted state in the tooth zone of the jaws.

Figure 13:
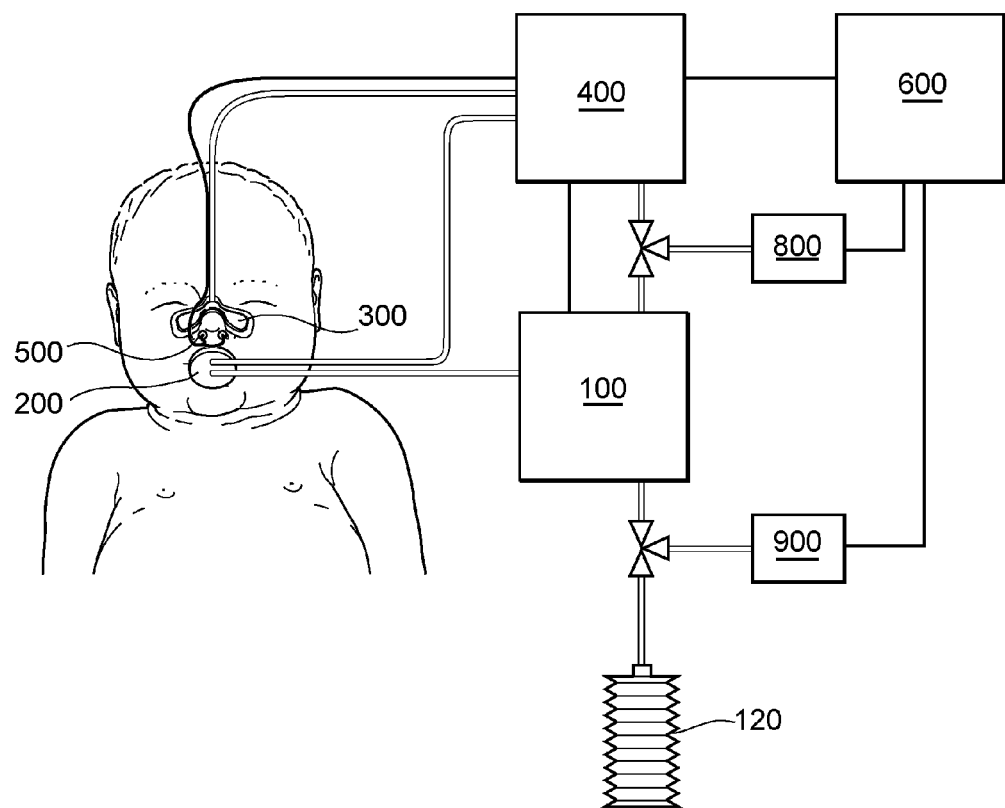
FIG. 13 schematically shows an embodiment where a device 800 for detecting a first component in exhaled air is connected to the conduit leading to the flow generator 400, and where a sample bag 120 and a device 900 for detecting a one or more further component(-s) in exhaled air can be connected to the sample collector 100.

FIG. 13 schematically shows an embodiment where a device 800 for detecting a first component in exhaled air is connected to the conduit leading to the flow generator 400, and how a sample bag 120 and a device 900 for detecting a second component in exhaled air can be connected to the sample collector 100, for example a NO analyzer.

The first component can be oxygen or carbon dioxide, and the determination of any of these can be used to determine the origin of the exhalation air, knowing that air originating from the lungs will contain significantly less oxygen and more carbon dioxide than air originating from the dead space, e.g. the oral cavity and the airways excluding the lung.

When the second component to be determined is NO, the device 900 may be a NO analyzer operating based on chemiluminescence, semiconductor-based sensors, electrochemical sensors, or polymer-based sensors. In the set-up according to the embodiment shown in FIG. 11, it is conceived that the flow generator 400 communicates also with the analyzer 900, for example initiating the analysis. The components can communicate as indicated in the figure, or in different configurations, for example via the interface 600, either wirelessly or via cables.

The invention also makes available a method of collecting samples of exhaled air during normal respiration conditions, comprising the steps of:
  detecting a change in a parameter representing the change from inhalation to exhalation and transmitting said change as a signal;
  receiving said signal in a control unit;
  activating a device for isolating the nasal airways;
  activating a flow generator connected to an exhalation air receiver; and
  collecting a sample of exhaled air during exhalation when the nasal airways are isolated.

According to a preferred embodiment, the method further comprises a step of deactivating the device for isolating the nasal airways when the end of an exhalation and/or the beginning of an inhalation is detected.

According to preferred embodiment, freely combinable with any of the methods disclosed herein, the detection of the inhalation and the beginning of the exhalation is based on the detection/measurement of one or more of oral pressure, flow of air in the airways, movements of the thorax and/or abdomen, electrical impulses as a sign of respiratory activity.

Further, according to an embodiment of the method, the device for isolating the nasal airways is activated when the beginning of exhalation is detected, or a preset period of time after the detection of the beginning of exhalation.

Preferably the aspiration of a sample of exhaled air takes place when the beginning of exhalation is detected, or when a preset period of time has elapsed from the detection of the beginning of exhalation.

Preferably, according to an embodiment of the method, the device for isolating the nasal airways is deactivated, and the aspiration of a sample of exhaled air interrupted, when a preset period of time has elapsed from the detection of the beginning of exhalation.

Preferably said preset time is determined on the basis of measured values for a normal respiration cycle. Said preset time can also be determined continuously, and repeated for each further breath depending, thus allowing for the aspiration to adapt to the current breathing rhythm. Similarly, a preset volume is determined on the basis of measured values for a normal respiration cycle.

Preferably, according to an embodiment of the method, the device for isolating the nasal airways is deactivated, and the aspiration of a sample of exhaled air interrupted when an inhalation phase of the next breathing cycle is detected.

According to an embodiment of the method, freely combinable with any other embodiment disclosed herein, the exhalation receiver is introduced orally and positioned with at least one inlet opening for exhalation air in the rear pharyngeal space.

Further, in a method according to any embodiment disclosed herein, a sample of exhalation air is collected during one or several breathing cycles.

Preferably the determination of a normal respiration cycle is based on the detection/measurement of one or more of oral pressure, flow of air in the airways, movements of the thorax and/or abdomen, and electrical impulses (impedance) as a sign of respiratory activity.

Preferably deviations from the normal respiration that indicate a premature inhalation bring about an interruption of the aspiration and a deactivation of the device for isolating the nasal airways. In addition, prior to the beginning of the next, spontaneously performed inhalation phase of the next breathing cycle the removal of the exhaled air by aspiration is interrupted in a time-controlled manner and/or in a manner controlled by the measured values, whereby at the same time the means for closing the velum and/or nose is deactivated. The latter allows the child to inhale undisturbed.

According to one embodiment, freely combinable with any other embodiment disclosed herein, the beginning of the relevant portion of the exhalation air is detected by determining the O2 or the CO2 content of the exhaled air by a O2 or a CO2 analyzer to which the exhaled air is supplied.

This method step makes use of the fact that the concentration of CO2 in the exhaled air is higher than in the inhaled air. The beginning of a relevant part of the exhalation can therefore be determined by determining the CO2 content of the exhaled air by a CO2 analyzer. To this end the exhaled air is supplied to a CO2 analyzer that determines the concentration values and supplies them as signals to a control unit where they are evaluated. After a comparison of actual values and theoretical values of the CO2 content or of the fluctuations of the concentration, the start of the exhalation can be determined and the aspiration of a sample initiated.

According to another embodiment, freely combinable with any other embodiment disclosed herein, the sample of exhaled air is subjected to a qualitative or quantitative analysis of a component chosen from scientifically and/or clinically interesting components. Two examples of clinically interesting components in exhaled air are inorganic and organic gaseous compounds. Examples of gaseous compounds present in exhaled air include nitrogen monoxide, here nitric oxide (NO), carbon dioxide (CO2), oxygen (O2), and volatile organic compounds. Further examples are more or less complex chemical compounds and biomolecules that can be detected in exhaled breath condensate, such as hydrogen peroxide, S-nitrosothiols, nitrotyrosine, proteins, cytokines, and macromolecules, to mention only a few.

Preferably the sample of exhaled air is subjected to a quantitative analysis of the concentration of nitric oxide. The analysis of NO can be take place using chemiluminescence, semiconductor-based sensors, electrochemical sensors, or polymer-based sensors.

Most preferably the concentration of nitric oxide is determined in the sample of exhaled air, and wherein the parameters of the exhalation during which a sample is aspirated are controlled to values as set out in the ATS/ERS guidelines 2011.

The invention claimed is:

1. An apparatus for collection of samples of exhaled air during respiration of a subject, said subject having a nose, a root and apex of said nose, nasal airways comprising nostrils and a vestibule and atrium of said nostrils, a mouth, lips, an oral cavity, and a pharyngeal cavity comprising a soft palate and pharynx, the apparatus comprising a sample collector, an exhalation air receiver, and a device for isolating the nasal airways, wherein the apparatus further comprises:

at least one sensor for detecting a change in a parameter representing a change from inhalation to exhalation and to transmit said change as a signal;

a flow generator;

a control unit adapted to receive said signal and to control said device for isolating the nasal airways, and to control the flow generator to create a flow of exhaled air through the sample collector; wherein the flow generator is in fluid communication with the sample collector; and the sample collector is in fluid communication with or integrated with the exhalation air receiver;

wherein the device for isolating the nasal airways comprises a means for blocking the passage of air through the nasal airways, said means comprising inflatable pads adapted for placing on the outside of the nose between the root and the apex of the nose, wherein the inflatable pads in an inflated state compress the vestibule and/or atrium of both nostrils blocking the passage of air through the nasal airways.

2. The apparatus according to claim 1, wherein the exhalation air receiver comprises an elongated, hollow structure having a body for insertion into the oral cavity; with at least one inlet opening for exhalation air adapted to be positioned in the pharyngeal cavity, and an outlet opening adapted to be positioned outside the lips; wherein said at least one inlet opening communicates with the outlet opening via a hollow space of the body or via a tubing through the body, and the outlet opening is connected to the flow generator.

3. The apparatus according to claim 1, wherein said at least one sensor for detecting an inhalation and at least a beginning of an exhalation is chosen from an optical sensor, a temperature sensor, a flow meter, a pressure sensor, an impedance meter, an EEC electrode, a humidity sensor, an expansion meter, a piezoelectric sensor, an acoustic sensor, or any combination thereof.

4. The apparatus according to claim 1, wherein the flow generator comprises a gas-impermeable collection bag surrounded by a container, wherein the container can be evacuated, producing a vacuum in order to aspire a sample into said collection bag.

5. The apparatus according to claim 1, wherein the flow generator comprises a pump or fan, adapted for accurately maintaining a flow in the range of 1-100 ml/s.

6. The apparatus according to claim 1, wherein the device for isolating the nasal airways comprises an orally insertable expandable body which, when in place in the oral cavity and positioned under the soft palate, in expanded state pushes the soft palate in a dorsocranial direction, preventing air from passing between the nasal airways and the pharynx.

* * * * *